US010863932B1

(12) United States Patent
Kam

(10) Patent No.: US 10,863,932 B1
(45) Date of Patent: Dec. 15, 2020

(54) POROUS MICRONEEDLES THROUGH SACRIFICIAL SUGAR INCORPORATION, ANALYTE DETECTION SYSTEM, AND METHOD FOR INTRADERMAL OPTODE NANOSENSOR IMPLANTATION

(71) Applicant: Verily Life Sciences LLC, Mountain View, CA (US)

(72) Inventor: Kimberly Kam, Mountain View, CA (US)

(73) Assignee: Verily Life Sciences LLC, Mountain View, CA (US)

( * ) Notice: Subject to any disclaimer, the term of this patent is extended or adjusted under 35 U.S.C. 154(b) by 239 days.

(21) Appl. No.: 16/126,205

(22) Filed: Sep. 10, 2018

Related U.S. Application Data

(62) Division of application No. 14/793,220, filed on Jul. 7, 2015, now Pat. No. 10,098,574.

(51) Int. Cl.
*A61B 5/1455* (2006.01)
*A61B 5/145* (2006.01)

(52) U.S. Cl.
CPC ........ *A61B 5/14514* (2013.01); *A61B 5/1455* (2013.01); *A61B 5/14546* (2013.01)

(58) Field of Classification Search
None
See application file for complete search history.

(56) References Cited

U.S. PATENT DOCUMENTS 2,784,127 A 3/1957 Joyner et al.
4,444,933 A 4/1984 Columbus et al.
6,503,231 B1 1/2003 Prausnitz et al.
(Continued)

FOREIGN PATENT DOCUMENTS

CA 2 436 207 C 9/2002
EP 1877863 A2 1/2008
(Continued)

OTHER PUBLICATIONS

Greene, H., "Cotton Candy Capillaries", Biomedical Engineering, University of Rhode Island, BME 281 First Presentation, Oct. 4, 2011, <hrgreene2@my.uri.edu>, 14 pages.
(Continued)

*Primary Examiner* — Marjan Fardanesh
(74) *Attorney, Agent, or Firm* — McDonnell Boehnen Hulbert & Berghoff LLP

(57) ABSTRACT

A device and system for measuring and/or monitoring an analyte present on the skin is provided. The system includes a skin-mountable device that may be attached to an external skin surface and a reader device. The skin-mountable device includes a substrate, a plurality of micro-needles, and nanosensors encapsulated in the micro-needles. The micro-needles are attached to the substrate such that attachment of the substrate to an external skin surface causes to the micro-needles to penetrate into the skin to contact interstitial fluid. The micro-needles can include a sacrificial agent and are configured to become porous on contact with a solvent, e.g., interstitial fluid, which dissolves at least a portion of the sacrificial agent. The nanosensors encapsulated in the micro-needles include a detectable label and are configured to interact with a target analyte present in the interstitial fluid. The reader device is configured to detect the analyte in interstitial fluid via interaction with the skin-mountable device.

10 Claims, 7 Drawing Sheets

(56) References Cited

U.S. PATENT DOCUMENTS

| | | | |
|---|---|---|---|
| 7,344,499 | B1 | 3/2008 | Prausnitz et al. |
| 7,494,557 | B1 | 2/2009 | Peterson |
| 7,785,301 | B2 | 8/2010 | Yuzhakov |
| 8,016,853 | B2 | 9/2011 | Griffen et al. |
| 8,070,718 | B2 | 12/2011 | Weber et al. |
| 8,236,342 | B2 | 8/2012 | Thomas et al. |
| 8,263,358 | B2 | 9/2012 | Clark et al. |
| 8,357,616 | B2 | 1/2013 | Linder et al. |
| 8,470,300 | B2 | 6/2013 | Clark et al. |
| 8,708,966 | B2 | 4/2014 | Allen et al. |
| 8,765,458 | B2 | 7/2014 | Clark et al. |
| 10,098,574 | B1 | 10/2018 | Kam |
| 2002/0138049 | A1 | 9/2002 | Allen et al. |
| 2008/0275318 | A1 | 11/2008 | Lastovich et al. |
| 2010/0240117 | A1 | 9/2010 | Ying et al. |
| 2011/0184259 | A1 | 7/2011 | Alarcon et al. |
| 2011/0224515 | A1 | 9/2011 | Mir et al. |
| 2011/0270412 | A1 | 11/2011 | Bellan et al. |
| 2012/0323211 | A1 | 12/2012 | Ogle et al. |
| 2013/0190839 | A1 | 7/2013 | Rapsey et al. |
| 2014/0188033 | A1 | 7/2014 | Rapsey et al. |
| 2014/0255311 | A1 | 9/2014 | Almutairi et al. |
| 2014/0275843 | A1 | 9/2014 | Piccirillo et al. |

FOREIGN PATENT DOCUMENTS

| | | | |
|---|---|---|---|
| EP | 2 439 227 | B1 | 6/2013 |
| WO | 00/74763 | A2 | 12/2000 |
| WO | 2006065312 | A1 | 6/2006 |
| WO | 2006113492 | A2 | 10/2006 |
| WO | 2009/040548 | A1 | 4/2009 |
| WO | 2009/051703 | A1 | 4/2009 |
| WO | 2010/051551 | A1 | 5/2010 |
| WO | 2013108234 | A1 | 7/2013 |
| WO | 2013/134401 | A2 | 9/2013 |

OTHER PUBLICATIONS

Li, V., "From Cotton Candy to Capillaries", The Cornell Daily Sun, Mar. 25, 2009, 1 page.

He, Y., et al., "Printing 3D Microfluidic Chips with a 3D Sugar Printer", Microfluidics and Nanofluidics, Apr. 2, 2015, pp. 1-9, DOI:10.1007/s10404-015-1571-7. (Abstract only).

"Laboratory for Bioregenerative Medicine and Surgery", pp. 1-2. [Retrieved from Wikipedia May 4, 2015:<URL:http://en.wikipedia.org/wiki/Laboratory_for_Bioregenerative_Medicine_and_Surgery>].

"Tissue Engineering", pp. 1-14. [Retrieved from Wikipedia May 4, 2015:<URL:http://en.wikipedia.org/wiki/Tissue_engineering>].

Balaconis, et al., "Biodegradable Optode-based Nanosensors for In-Vivo Monitoring", Anal. Chem., Jul. 3, 2012, vol. 84(13), pp. 5787-5793, doi:10.1021/ac301137c.

Billingsley, et al., "Fluorescent Nano-Optodes for Glucose Detection", Anal. Chem., May 1, 2010, vol. 82(9), pp. 3707-3713, doi:10.1021/ac100042e.

Clark, et al., "Optochemical Nanosensors and Subcellular Applications in Living Cells", Mikrochimica Acta, 1999, vol. 131, pp. 121-128.

Monson, et al., "PEBBLE Nanosensors for In Vitro Bioanalysis", Biomedical Photonics Handbook, T. Vo-Dinh, editor, CRC Press, Boca Raton, FL (2003), www.umich.edu/-koplab/research2/CRC_Review_try3pr.pdf, 9 pages.

Ruckh, et al., "Polymer-Free Optode Nanosensors for Dynamic, Reversible, and Ratiometric Sodium Imaging in the Physiological Range", Scientific Reports, Nov. 28, 2013, vol. 3(3366), pp. 1-12, doi:10.1038/srep03366.

Soppimath, et al., "Biodegradable Polymeric Nanoparticles as Drug Delivery Devices", Journal of Controlled Release, 2001, vol. 70, pp. 1-20.

Dick, Lisa, "Pointing the Way", Innovations in Pharmaceutical Technology, 2014, Issue 50, pp. 1-3.

McIntyre, David, "Optical Tweezer Trapping of Fluorescent Ion Nanosensors", Oregon State University, pp. 1-3. [Retrieved from the Internet Oct. 21, 2014:<URL:http://www.physics.oregonstate.edu/-mcintyre/optodes.html>].

Prausnitz, Mark, "Polymer Microneedles", Laboratory for Drug Delivery, 2010, pp. 1-5. [Retrieved from the Internet Oct. 14, 2014:<URL:http://drugdelivery.chbe.gatech.edu/gallery_microneedles.html>].

Robinson-Avila, Kevin, "Sandia Develops Wrist Sensor for Electrolytes", Albuquerque Journal News, Jun. 16, 2014, pp. 1-2.

"Microneedle Drug Delivery Systems", 3M Drug Delivery Systems, pp. 1-3 [Retrieved from the Internet Oct. 14, 2014:<URL:http://solutions.3m/en_WW/3M-DDSD/Drug-Delivery-Systems/Technologies/Microneedle>].

"3M Hollow Microstructured Transdermal System", 3M Drug Delivery Systems, 2014, pp. 1-2.

"Technologies—Micro-Trans", Valeritas, 1 page.

Burton, et al., "Rapid Intradermal Delivery of Liquid Formulations Using a Hollow Microstructured Array", Pharm. Res., Jun. 26, 2010, pp. 1-10, doi:10.1007/sII095-010-0177-8.

Cash, et al., "Nanosensors and Nanomaterials for Monitoring Glucose in Diabetes", Trends Mol. Med., Sep. 23, 2010, vol. 16(12), pp. 584-593, doi: 10.1016/j.molmed.2010.08.002.

Dubach, et al., "Fluorescent Nanoparticles for the Measurement of Ion Concentration in Biological Systems", J. Vis. Exp., Jul. 4, 2011, vol. 53, p. 1-8, doi:10.3791/2896.

POROUS MICRONEEDLES THROUGH SACRIFICIAL SUGAR INCORPORATION, ANALYTE DETECTION SYSTEM, AND METHOD FOR INTRADERMAL OPTODE NANOSENSOR IMPLANTATION

CROSS-REFERENCE TO RELATED APPLICATIONS

This application is a division of U.S. patent application Ser. No. 14/793,220, filed Jul. 7, 2015, which is incorporated herein by reference.

BACKGROUND

Unless otherwise indicated herein, the materials described in this section are not prior art to the claims in this application and are not admitted to be prior art by inclusion in this section.

A number of scientific methods have been developed to detect and/or measure one or more analytes in a person's blood. The presence or absence of a physiologically relevant analyte in the blood, or the presence at a particular concentration or range of concentrations, may be indicative of a medical condition or the person's state of health. Physiologically relevant analytes may include enzymes, hormones, proteins, cells or other molecules.

In a typical scenario, a person's blood is drawn and sent to a lab where a variety of tests are performed to measure various analyte levels and parameters in the blood. The variety of tests may be referred to as "blood work," where the blood is tested for the presence of various diseases, or analyte levels such as cholesterol levels, etc. For most people, the blood tests are infrequent, and an abnormal analyte level indicative of a medical condition may not be identified for some time after the blood work is performed. Physiologically relevant analytes may also be present in a person's interstitial fluid. These analytes include sugars, salts, fatty acids, amino acids, coenzymes, hormones, neurotransmitters, and cell waste products. In analyzing for the presence and/or concentration of analytes from blood and other fluids, hypodermic needles are typically used which can cause pain, wounds, and potential infection sites in patients. A device and method that avoids the use of hypodermic needles and reduces the need for medical personnel and administration costs is desirable.

SUMMARY

One aspect of the present disclosure provides a device. The device includes a plurality of micro-needles, each micro-needle having a base end and a tip, wherein the micro-needles comprise a sacrificial agent and wherein the micro-needles are configured to become porous on contact with interstitial fluid by dissolution of at least a portion of the sacrificial agent; a substrate attached to the base ends of the micro-needles, wherein the substrate is configured for attachment to an external skin surface such that the micro-needles penetrate into the skin to contact interstitial fluid; and nanosensors encapsulated in the micro-needles, the nanosensors comprising nanoparticles having a detectable label and configured to interact with a target analyte present in interstitial fluid.

In some embodiments, the micro-needles are arranged in an array. In other embodiments, the sacrificial agent, e.g., sacrificial sugar, is encapsulated in the micro-needles. In some embodiments, the micro-needles include an enclosed hollow space. The nanosensors can be encapsulated in a hydrogel present in the enclosed hollow space. In some embodiments, the detectable label comprises a fluorophore. In some embodiments, the substrate further includes an adhesive material for attaching the substrate to the external skin surface, for attaching the base ends of the micro-needles to the substrate, or both. In some embodiments, the adhesive can be water-soluble such that the substrate can be detached from the base end of the micro-needles and from the external skin surface. In some embodiments, the micro-needles, the nanosensors, or both are biodegradable. In some embodiments, the micro-needles comprise a biodegradable polymer. In some embodiments, the micro-needles are solid.

In another aspect, a device is provided. The device includes a plurality of micro-needles, each micro-needle having a base end and a tip, wherein the micro-needles comprise pores; a substrate attached to the base ends of the micro-needles, wherein the substrate is configured for attachment to an external skin surface such that the micro-needles penetrate into the skin to contact interstitial fluid; and nanosensors encapsulated in the micro-needles, wherein the nanosensors comprise nanoparticles having a detectable label and configured to interact with a target analyte present in interstitial fluid, and wherein the pores are configured to allow at least a portion of the nanosensors to be in fluid contact with the interstitial fluid.

In another aspect, a system is provided. The system includes (a) a skin-mountable device, comprising: a plurality of micro-needles, each having a base end and a tip, wherein the micro-needles comprise a sacrificial agent and wherein the micro-needles are configured to become porous in response to exposure to a liquid that dissolves at least a portion of the sacrificial agent; a substrate attached to the base ends of the micro-needles, wherein the substrate is configured for attachment to an external skin surface such that the micro-needles penetrate into the skin to contact interstitial fluid; and nanosensors encapsulated in the micro-needles, the nanosensors comprising nanoparticles having a detectable label and configured to interact with a target analyte present in interstitial fluid; and (b) a reader device, wherein the reader device is configured to detect the target analyte via interaction with the skin-mountable device.

In other embodiments, the substrate includes a component configured to undergo an optically-detectable change upon interaction with an analyte. The optically-detectable change may involve a change in at least one of optical absorption, reflectivity, or fluorescence. The substrate can be used in conjunction with a reader device configured to detect the optically-detectable change. The reader device may include an excitation light source configured to direct light toward the substrate, and a photodetector configured to detect light from the substrate. The detected optical change can be used to determine the presence/absence of an analyte or the concentration of an analyte.

In another aspect, a system is provided. The system includes: (a) a skin-mountable device, comprising: a plurality of micro-needles, each having a base end and a tip, wherein the micro-needles comprise pores; a substrate attached to the base ends of the micro-needles, wherein the substrate is configured for attachment to an external skin surface such that the micro-needles penetrate into the skin to contact interstitial fluid; and nanosensors encapsulated in the micro-needles, wherein the nanosensors comprise nanoparticles having a detectable label and configured to interact with a target analyte present in interstitial fluid; and wherein the pores are configured to allow at least a portion of the nanosensors to be in fluid contact with the interstitial fluid;

and (b) a reader device, wherein the reader device is configured to detect the target analyte via interaction with the skin-mountable device. In some embodiments, the micro-needles further comprise an enclosed hollow space, and wherein the nanosensors are encapsulated in a hydrogel present in the enclosed hollow space.

In another aspect, the present disclosure provides a method. The method includes transmitting incident light from a reader device to a skin-mountable device, wherein the skin-mountable device comprises (i) a plurality of micro-needles, each having a base end and a tip, wherein the micro-needles comprise a sacrificial agent and wherein the micro-needles are configured to become porous in response to exposure to a liquid that dissolves at least a portion of the sacrificial agent, (ii) a substrate attached to the base ends of the micro-needles, wherein the substrate is configured for attachment to an external skin surface such that the micro-needles penetrate into the skin to contact interstitial fluid, and (iii) nanosensors encapsulated in the micro-needles, the nanosensors comprising nanoparticles having a fluorophore and configured to interact with a target analyte present in interstitial fluid; receiving, by the reader device, fluorescence light emitted by the nanosensors interacting with the target analyte in response to the incident light; and detecting the target analyte based on the fluorescence light received by the reader.

In some embodiments, the sacrificial agent includes a sacrificial sugar. In some embodiments, the sacrificial sugar is encapsulated in the micro-needles. In some embodiments, detecting the target analyte based on the fluorescence light received by the reader comprises determining a concentration of the target analyte in the interstitial fluid based on the fluorescence light received by the reader. In some embodiments, the substrate comprises a polymeric material transparent to the incident light and the fluorescence light.

In another aspect, the present disclosure provides another method. The method includes: transmitting incident light from a reader device to a skin-mountable device, wherein the skin-mountable device comprises (i) a plurality of micro-needles, each having a base end and a tip, wherein the micro-needles comprise pores, (ii) a substrate attached to the base ends of the micro-needles, wherein the substrate is configured for attachment to an external skin surface such that the micro-needles penetrate into the skin to contact interstitial fluid, and (iii) nanosensors encapsulated in the micro-needles, wherein the nanosensors comprise nanoparticles having a fluorophore and configured to interact with a target analyte present in interstitial fluid, and wherein the pores are configured to allow at least a portion of the nanosensors to be in fluid contact with the interstitial fluid; receiving, by the reader device, fluorescence light emitted by the nanosensors interacting with the target analyte in response to the incident light; and detecting the target analyte based on the fluorescence light received by the reader.

In some embodiments, the micro-needles are biodegradable, biocompatible, or both. In other embodiments, the micro-needles are not biodegradable.

These as well as other aspects, advantages, and alternatives, will become apparent to those of ordinary skill in the art by reading the following detailed description, with reference where appropriate to the accompanying drawings.

DETAILED DESCRIPTION

I. Overview

Figure 1:
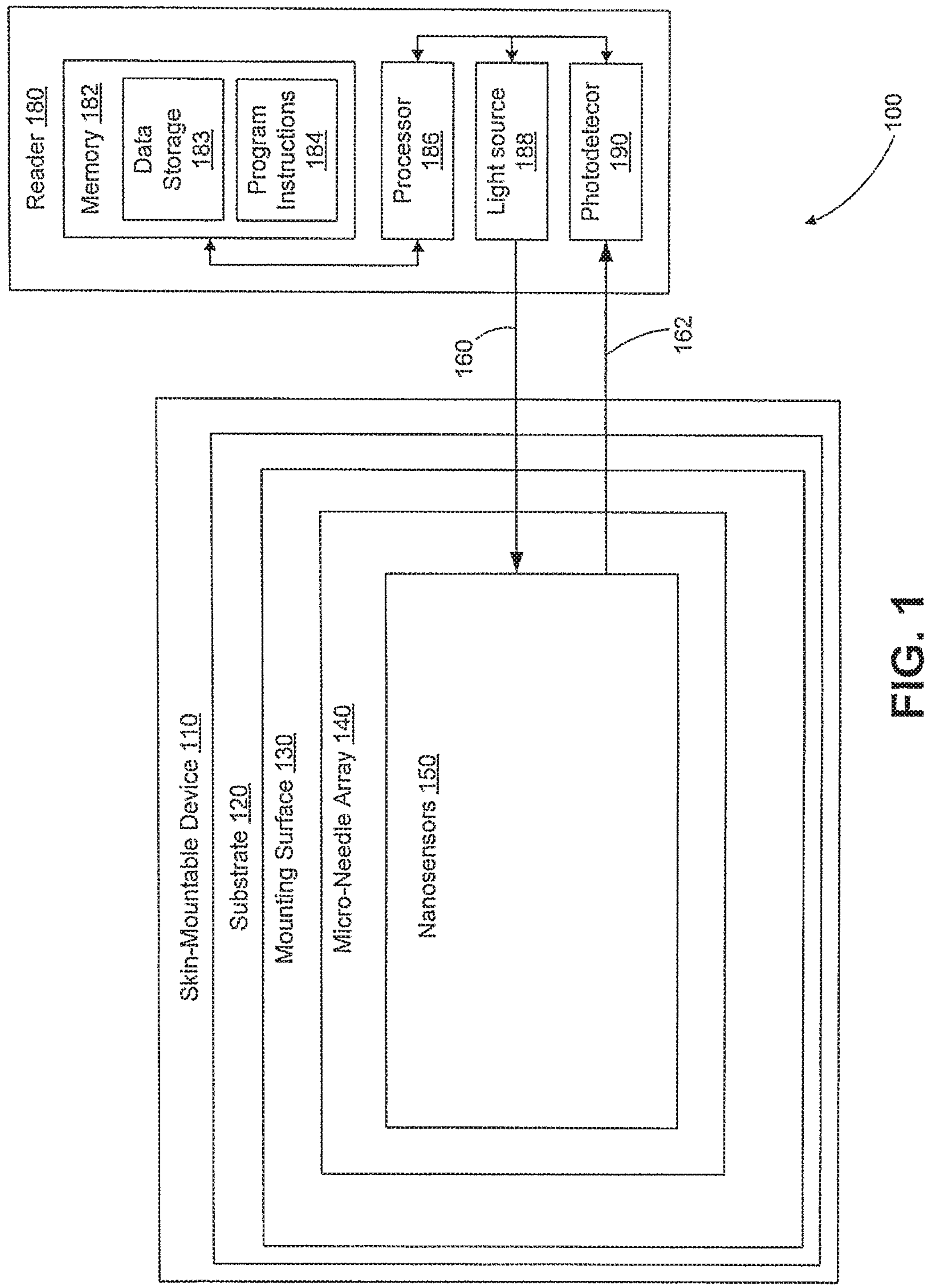
FIG. 1 is a block diagram of an example system that includes a skin-mountable device in wireless communication with a reader device, in accordance with an example embodiment.

A system for monitoring analyte levels can include a skin-mountable device and a reader device. The skin-mountable device may include a plurality of micro-needles that can penetrate into the epidermis, intradermis, or dermis, a polymer backing attached to the micro-needles, and optode nanosensors configured to interact with an analyte present in interstitial fluid in the skin. The micro-needles are porous or are configured to become porous when exposed to interstitial fluid upon implantation. The reader device can detect the analyte by optically interrogating the nanosensors. Alternatively or additionally, the skin-mountable device may include its own optical sensor, control electronics, and an antenna for wireless communication with the reader. The control electronics can operate the sensor to perform readings and can operate the antenna to wirelessly communicate the readings from the sensor to the reader device via the antenna.

A "skin-mountable" device or substrate can be attached to an "external skin surface," i.e., the epidermis, intradermis, or dermis, and in that attached position the micro-needles can penetrate into subsurface skin tissue, i.e. the epidermis, intradermis, or dermis. In this way, the micro-needles may have direct contact with interstitial fluid. In one embodiment, the substrate can be a transdermal micro-needle patch.

Interstitial fluid contains a variety of inorganic electrolytes (e.g., $Na^+$, $Ca^{2+}$, $K^+$, bicarbonate, $Cl^-$), organic components (e.g., glucose, urea, creatinine), and so on that can be used to diagnose health states. A system including the above-mentioned nanosensors can be configured to measure one or more of these analytes can thus provide a convenient platform useful in diagnosing and/or monitoring health states. For example, a system can be configured to sense glucose and can be used by diabetic individuals to measure/monitor their glucose levels.

An external reader device or "reader" can optically interrogate the skin-mountable device. For example, the reader can transmit incident light that excites a fluorophore in the nanosensors and receive fluorescence light from the nanosensors interacting with the target analyte. The reader may detect the target analyte (and may determine the concentration of the target analyte in the interstitial fluid) based on the fluorescence light.

The analyte concentration information can be sent from the reader to a display device. The display device could be, for example, a wearable, laptop, desktop, handheld, or tablet computer, a mobile phone, or a subsystem of such a device. In some embodiments, the reader is also the display device. The display device can include a processing system; e.g., a central processing unit (CPU), and a non-transitory computer readable medium configured to store at least program instructions. One example of a wearable computer is a head-mountable display (HMD). The HMD can be a device that is capable of being worn on the head and places a display in front of one or both eyes of the wearer. The display device can store the data received from the reader, perhaps process the data, and generate display(s) based on the received and/or processed data.

In some embodiments, the reader is a wearable device, such as an arm or wrist band, and can be worn directly over the skin-mountable device.

II. Example System

FIG. 1 is a block diagram of a system 100 that includes a skin-mountable device 110 and a reader 180. The skin-mountable device 110 includes a substrate 120 that is configured to be mounted to an external body surface (i.e., skin). The substrate 120 could be formed from a polymeric material, for example. The substrate 120 has a mounting surface 130 for mounting to the skin. Attached to the mounting surface 130 of the substrate is a micro-needle array 140. The micro-needle array 140 is configured to penetrate into the skin (e.g., into the intradermis when the substrate 120 is mounted to the skin. Disposed within the micro-needles of the array 130 are nanosensors that are sensitive to a target analyte present in interstitial fluid in the epidermis, intradermis, or dermis. The nanosensors are in the form of nanoparticles and include a detectable label (e.g., fluorophore). The optical properties of the detectable label undergo a detectable change (e.g., a change in fluorescence) when the nanosensor interacts with the target analyte. In one embodiment, the micro-needles are porous and are configured such that the interstitial fluid is in contact with at least a portion of the nanosensors encapsulated in the micro-needles. In another embodiment, the micro-needles include a sacrificial agent and are configured to become porous in response to interstitial fluid that dissolves at least a portion of the sacrificial agent. The interstitial fluid can then interact with the nanosensors encapsulated in the micro-needles.

Reader 180 can also include a computing system with a processor 186 in communication with a memory 182. Memory 182 is a non-transitory computer-readable medium that can include, without limitation, magnetic disks, optical disks, organic memory, and/or any other volatile (e.g. RAM) or non-volatile (e.g. ROM) storage system readable by the processor 186. The memory 182 can include a data storage 183 to store indications of data, such as sensor readings (e.g., from the analyte bio-sensor 162), program settings (e.g., to adjust behavior of the substrate 110 and/or reader 180), etc. The memory 182 can also include program instructions 184 for execution by the processor 186 to cause the reader 180 to perform processes specified by the instructions 184. For example, the program instructions 184 can cause reader 180 to perform any of the operations described herein.

As shown, the reader device 180 can include a light source 188 configured to transmit incident light 160 to the skin-mountable device 110 and a photodetector 190 configured to receive light 162 from the skin-mountable device 110. The incident light 160 can be used to optically interrogate the nanosensors 150 so as to detect interaction of the nanosensors 150 with the target analyte in the interstitial fluid. For example, the incident light can include a wavelength that excites a fluorophore in the nanosensors 150 such that the nanosensors 150 emit fluorescence light. The fluorescence light can be included in the received light 162 and detected by the photodetector 162. Based on the light from the nanosensors 150 that is detected by the photodetector 160, the reader 180 can detect the target analyte. Moreover, the detection could be quantitative. For example, an intensity, wavelength, or other characteristic of the received light 162 may be indicative of the concentration of the target analyte in the interstitial fluid.

The components of the skin-mountable device 110 may be transparent to the incident light 160 and the light 162 emitted by the nanosensors in response to the incident light 160.

III. Illustrative Micro-Needle Sensor

Interstitial fluid flow poses a challenge for the implantation of optode nanosensors because of the rapid particle diffusion from the injection site. Rapid particle diffusion causes a loss of fluorescence intensity due to nanosensor migration. Additionally, in vivo implantation of the nanosensors can induce biofouling and initiate the wound healing response which could attenuate the nanosensor sensitivity. One potential solution to these challenges would be to embed the fluorescent nanoparticles into porous biocompatible and/or biodegradable micro-needles as described in the present disclosure. The resulting micro-needles would provide the following benefits: (a) allowing for an array that would provide a spatially controlled implantation of the nanosensors and prevent nanosensor migration from the implant site; (b) the biocompatible/biodegradable material would protect the nanosensors against biofouling and the wound healing process; and (c) the porosity of the micro-needles would provide channels to allow for uninhibited diffusion of analytes such as ions to diffuse into the micro-needles to interact with the protected nanosensors. Typically, diffuse hydrogels are used for this purpose, however, hydrogels are not stiff enough to penetrate the skin. By creating porous channels in the micro-needles, both the diffusion of the analyte of interest into the micro-needles and adequate material stiffness for skin penetration are possible.

In one aspect, a transdermal or skin patch is provided. The skin patch having an array of microfabricated micro-needles can be used as a minimally invasive device for detecting target analytes in interstitial fluid or for delivering nanosensors into the skin for detecting target analytes. Thus, in one embodiment, the micro-needles can act as a sensing element. A skin patch having micro-needle array would allow for a spatially-controlled array of optode nanosensors to be implanted at a controlled depth into the epidermis, intradermis, or dermis, allowing for an optimal depth to be selected, e.g., depending on the individual's specific physiology, to sample interstitial fluid. As defined herein, "optode nanosensors" or "nanosensors" refers to nanosensors that emit an optical signal, e.g. fluorescent signal, indicative of detection of an analyte.

In some embodiments, the transdermal patch includes an array of microfabricated porous micro-needles having encapsulated nanosensors. The porous micro-needles that are configured such that the interstitial fluid can readily diffuse into the pores and interact with the nanosensors encapsulated in the micro-needles. In some embodiments, the nanosensors can be dispersed throughout the micro-needles or contained in a polymer matrix within an interior hollow space of the micro-needles.

In other embodiments, the transdermal patch includes an array of microfabricated micro-needles having encapsulated nanosensors. The micro-needles include a sacrificial agent that is configured to dissolve in the presence of interstitial fluid to form porous micro-needles. Upon implantation of the micro-needles and generation of porosity by the interaction of the micro-needles with interstitial fluid, the interstitial fluid can then interact with the nanosensors encapsulated in the micro-needles.

In some embodiments, the nanosensors are encapsulated in a polymer matrix contained in an interior hollow space of the micro-needles. The micro-needles include a sacrificial agent that is configured to dissolve in the presence of interstitial fluid to form porous micro-needles with channels that penetrate into the hollow interior space, exposing the nanosensors contained therein to interstitial fluid. Upon implantation of the micro-needles and generation of porosity via the interaction of the solid micro-needles and the interstitial fluid, the interstitial fluid can then diffuse interact with the nanosensors encapsulated in the hollow interior space in the micro-needles.

In another embodiment, the micro-needle array having nanosensors can be readily removed by simply removing the transdermal patch. In other embodiments, the micro-needle, the nanosensors, or both are made from biocompatible polymers. In other embodiments, the micro-needle array, the nanosensors, or both are made of biodegradable polymers. In other embodiments, the implanted micro-needle array having nanosensors can be left in place in the skin where both the micro-needle array and nanosensors are eventually degraded and absorbed.

The geometry of the micro-needles can be optimized to have a uniform cross-sectional area for accurate fluorescence detection as a function of depth. Furthermore, the micro-needle array would allow for single analyte or multiplex detection of different analytes such as potassium ions, sodium ions, glucose, using different nanosensors that are spatially well-defined. Furthermore, the micro-needle patch avoids the use of hypodermic needles for implantation as well as reduces the need for medical personnel and associated administration costs. The transdermal patch can be fabricated from or coated with FDA-approved biocompatible material to mitigate any inflammatory response. In one embodiment, the patch material can also be optically transparent to avoid interference with detection of the response signal by a photodetector.

In one embodiment, the transdermal patch includes an array of microfabricated micro-needles, the micro-needles having at least one type of nanosensor. The nanosensors can detect target analyte in interstitial fluid. In some embodiments, the micro-needles are porous. In other embodiments, the micro-needles include a sacrificial agent such that upon implantation, the interstitial fluid dissolves at least a portion of the sacrificial agent to generate porous micro-needles. The interstitial fluid can then interact with the nanosensors. In some embodiments, the nanosensors are encapsulated and dispersed throughout the micro-needles.

In other embodiments, the transdermal patch includes an array of microfabricated micro-needles having an interior hollow interior space, wherein the nanosensors are encapsulated in a polymer matrix contained in the hollow interior space. The polymer matrix of the hollow interior space can be the same or different from the polymer forming the micro-needles. The nanosensors can be bound covalently or non-covalently to the wall of the hollow interior space or to the polymer matrix within the hollow interior space. The micro-needles, the nanosensors, and/or the polymer matrix can be biodegradable.

In another embodiment, the microfabricated micro-needles can be biodegradable.

In another embodiment, the microfabricated micro-needles can be formed from a polymer that includes the nanosensors. The polymer matrix, the nanosensors, or both can be biodegradable.

In another embodiment, each micro-needle can be associated with a plurality of types of nanosensors, each type directed to a specific target analyte, to provide a spatially defined micro-needle array to allow for the detection of a multitude of different analytes such as $Na+$, $K+$, glucose, etc. in a controlled spatial array.

1. The Micro-Needle Sensor

The micro-needle sensor can include at least three components: (i) a plurality of micro-needle(s), (ii) a substrate to which the base of the micro-needles is secured or integrated, and (iii) at least one type of nanosensor. Optionally, a collection chamber for receiving interstitial fluid or a reservoir for delivering materials can be included. In one embodiment, the nanosensor can be coated, layered, or bound covalently or non-covalently to a surface of micro-needles. In some embodiments, the nanosensors can be suspended in a polymer matrix or gel contained within the interior hollow space of a solid or porous micro-needle. In other embodiments, the nanosensors are embedded in solid micro-needles. In another embodiment, at least one fluid collection chamber can be associated with the device for collecting interstitial fluid during detection of target analytes. Typically, the micro-needles are provided as a three-dimensional array, in contrast to a device with a single needle or row of needles. The micro-needle device can be adapted to be a single-use, disposable device, or can be adapted to be fully, or partially reusable.

a. Substrate

The substrate of the device can be constructed from a variety of materials, including metals, ceramics, semiconductors, organics, polymers, and composites. In one embodiment, the substrate can constructed with materials that are optically transparent so as to not interfere with optical detection of target analytes using the nanosensors.

The substrate includes an underlying surface to which the micro-needles are attached or integrally formed. A fluid collection chamber and/or reservoir can be attached to the substrate or formed (e.g., as part of the substrate) to communicate directly with the base of the micro-needles. In one embodiment, the substrate can be flexible so that it deforms with the skin and can assume a variety of shapes such as linear or curve shape to adapt to the elasticity of the skin.

In another embodiment, the substrate includes an adhesive material to temporarily secure the device to the skin surface. The adhesive can be essentially anywhere on the device to facilitate contact with skin. For instance, the adhesive can be anywhere on the substrate surface that contacts skin such as the surface of the substrate between the micro-needles near the base of the micro-needles. In one embodiment, the adhesive material is optically transparent so as to not interfere with the detection of the nanosensors.

In another embodiment, the substrate includes a water soluble adhesive material to temporarily secure the needles onto the substrate and to secure the device to the surface of the skin. After application of the micro-needle device to skin, water or an aqueous solution is then used to dissolve the adhesive and the substrate can be detached from the skin, releasing the needles into the skin. The needles remain stationary in a fixed position and this can allow for improved optical properties for detection. In some embodiments, the micro-needles are biodegradable so that they will degrade and disappear at a pre-determined time, e.g., three days or one week. In other embodiments, the nanosensors are biodegradable as well.

b. Micro-Needle Array

The array of micro-needles can function as a sensing element. When functioning as a sensing element, the nanosensors can be encapsulated in a polymer forming the micro-needles. The encapsulated nanosensors can be bound covalently or non-covalently to the polymer forming the micro-needles. The micro-needles can be porous or solid and can further have a hollow interior space. In some embodiments, the nanosensors are encapsulated in a polymer matrix that is contained in interior hollow spaces of the micro-needles. As used herein, the term "porous" means having pores or voids throughout at least a portion of the micro-needle structure, sufficiently large and sufficiently interconnected to permit passage of fluids into the micro-needle. As used herein, the term "hollow" means having one or more substantially annular bores or channels through the interior of the micro-needle structure, which have a diameter sufficiently large to permit passage of interstitial fluid into the micro-needle. The annular bores may extend through a portion of the needle in the direction of the tip to the base, extending parallel to the direction of the needle or branching or exiting at a side of the needle, as appropriate. One skilled in the art can select the appropriate porosity and/or bore features required for specific applications. For example, one can adjust the pore size or bore diameter to permit or regulate passage of the particular material to be transported into the micro-needle device.

In one embodiment, the micro-needles include a sacrificial agent. The micro-needles are configured to become porous on contact with a solvent, e.g., water or interstitial fluid, which at least partially or completely dissolves the sacrificial agent, creating voids, e.g., pores and/or channels, that would facilitate the diffusion of interstitial fluid into the micro-needles so that the analytes in the interstitial fluid can interact with the nanosensors. In some embodiments, the micro-needles are configured to become porous after implantation into skin wherein the interstitial fluid at least partially dissolves or completely dissolves the sacrificial agent.

In other embodiments, the micro-needles including the sacrificial agent are pre-treated with a solvent, e.g., water or an aqueous buffer solution, prior to implantation so as to at least partially or completely dissolve the sacrificial agent and form porous micro-needles. In some embodiments, devices including the porous micro-needles can be stored prior to use in implantation.

The micro-needles of the device can be constructed from a variety of polymeric materials, including biocompatible and/or biodegradable polymers. Representative polymers include, without limitation, biodegradable polymers of hydroxy acids such as lactic acid and glycolic acid polylactide, polyglycolide, polylactide-co-glycolide, and copolymers with PEG, polyanhydrides, poly(ortho)esters, polyurethanes, poly(butyric acid), poly(valeric acid), and poly (lactide-co-caprolactone). Representative non-biodegradable polymers include polycarbonate, polymethacrylic acid, ethylenevinyl acetate, polytetrafluoroethylene (TEFLON™), and polyesters. In one embodiment, the micro-needles can be constructed from materials that are optically transparent and do not interfere with the optical detection of target analytes.

A sacrificial agent or porogen can be incorporated before or during the solidification of the polymeric material used to form the micro-needles. The sacrificial agent is then later sacrificed such that it leaves voids, passages, or spaces, e.g., pores and/or channels in the micro-needles through which interstitial fluids could seep into and interact with the nanosensors after implantation. Representative sacrificial agents include, without limitation, any suitable material such as sugars, starches, cyclodextrin, salts such as NaCl, gelatin, alginates, a bio-resorbable materials, hyaluronic acid, waxes such as paraffin, low molecular weight water-soluble polymers, polyurethane, polyester, polyamide, polyacrylic acid (PAA), solvatable polymeric materials which are dispersible or soluble in water such as polyvinyl alcohol (PVOH), polyvinyl acetate (PVA) and so forth, and a material that is at least one of dissolvable and re-sorbable in the environment of the implant site. In some embodiments, the sacrificial agent can include a drug such as an antibiotic. In some embodiments, one or more sacrificial agents can be used. In other embodiments, two or more sacrificial agents can be used. In some embodiments, the size of the pores can be determined by the size of the particles of sacrificial agent. In general, the particle sizes range from 100 to 300 microns, depending on the sacrificial agent.

Any suitable amount of sacrificial agents can be incorporated into the polymer during formation of the micro-needles. The amount of sacrificial agents to include in the polymeric materials can generally range from about 5% to about 60%, usually from about 10% to about 40%. For preparing porous micro-needles prior to implantation, any suitable method for dissolving or leaching out the sacrificial agents from the micro-needles can be used including the use of a suitable solvent such as water, an alcohol, or other fluid. The sacrificial agent would be soluble in the solvent but not the polymer forming the micro-needles, thus forming voids, e.g., pores and/or channels, in the structure of the micro-needle following solvent treatment. In some embodiments, heat, sonic, ultrasonic vibration, or electromagnetic fields can be used to speed up the partial or complete dissolution of the sacrificial agent. In other embodiments, a solvent is applied to the micro-needles at a temperature of about 25 degrees Celsius to about 110 degrees Celsius.

In one embodiment, the micro-needles can have the mechanical strength to remain intact for sensing target analyte, while being inserted into the skin, while remaining in place for up to a number of days, and while being removed. In other embodiments where the micro-needles are formed of biodegradable polymers, the micro-needle can remain intact at least long enough for the micro-needle to serve its intended purpose (e.g., its sensing function). The micro-needles can be sterilizable using standard methods, such as ethylene oxide treatment or gamma irradiation.

The micro-needles can have straight or tapered shafts. In one embodiment, the diameter of the micro-needle is greatest at the base end of the micro-needle and tapers to a point or tip at the end distal the base. The micro-needle can also be fabricated to have a shaft that includes both a straight (untapered) portion and a tapered portion.

The cross-sectional dimensions of the micro-needles can be between about 1 μm and 500 μm, usually between 10 μm and 100 μm. The outer diameter can be between about 10 μm and about 100 μm, and the inner diameter can be between about 3 μm and about 80 μm. The length of the micro-needles can be typically between about 10 μm and 1 mm, usually between 100 μm and 500 μm or between 150 μm and 350 μm. The length is selected for the particular application, accounting for both an inserted and uninserted portion. One skilled in the art will understand that the proper selection of the length and diameter of the micro-needles depends on the skin depth that provides the greatest access of interstitial fluid and that pain avoidance from the micro-needles interacting with the nerve endings and capillaries in the dermis is desirable.

An array of micro-needles can include a mixture of micro-needles having, for example, various lengths, outer diameters, inner diameters, cross-sectional shapes, and spacings between the micro-needles. Generally, the micro-needles are sized to avoid or minimize contact with nerve endings in the biological tissue, such as the dermis, thereby eliminating or reducing pain when the micro-needles are inserted, for example into the skin.

The micro-needles can be oriented perpendicular or at an angle to the substrate. Preferably, the micro-needles are oriented perpendicular to the substrate to provide structural strength and to permit ease of insertion into the tissue. An array of micro-needles can include a mixture of micro-needle orientations, heights, spacings, or other parameters. This variation in an array can be useful, for example, if different micro-needles are to provide different sensing or insertion functions.

The micro-needle devices can be made by any suitable microfabrication processes, by creating small mechanical structures in polymer and other materials. These microfabrication processes are based on well-established methods used to make integrated circuits, electronic packages and other microelectronic devices, augmented by additional methods used in the field of micromachining. The micro-needle devices can have dimensions as small as a few nanometers and can be mass-produced at low per-unit costs. Representative microfabrication processes that may be used in making the micro-needles disclosed herein include lithography; injection molding; 3-D printing; etching techniques, such as wet chemical, dry, and photoresist removal; thermal oxidation of silicon; electroplating and electroless plating; diffusion processes, such as boron, phosphorus, arsenic, and antimony diffusion; ion implantation; film deposition, such as evaporation (filament, electron beam, flash, and shadowing and step coverage), sputtering, chemical vapor deposition (CVD), epitaxy (vapor phase, liquid phase, and molecular beam), electroplating, screen printing, lamination, stereolithography, laser machining, and laser ablation (including projection ablation).

In one embodiment, the interaction with the target analyte can occur in or on the micro-needle. In this embodiment, the nanosensor is located in the micro-needle, contacts the interstitial fluid containing the analyte, and undergoes a detectable change as a result of interaction with the analyte. The detectable change may be indicated optically, e.g., based on fluorescence emitted by the nanosensors when optically interrogated. The nanosensors can be located inside the surface of a porous micro-needle, and/or embedded within the micro-needle but exposed to interstitial fluid.

Figure 2A:
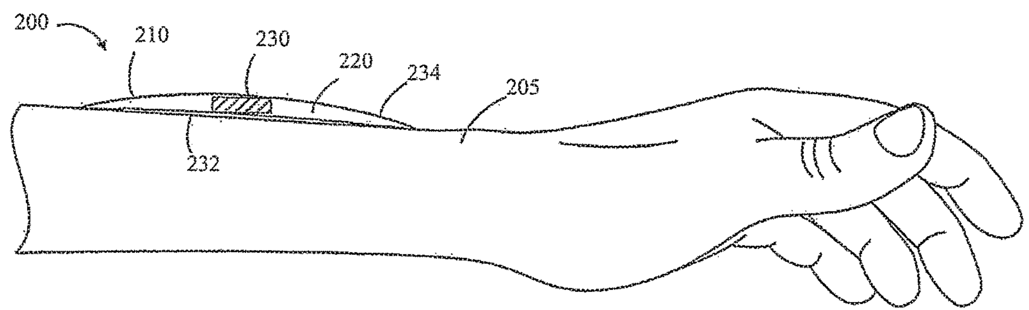
FIG. 2A is a side cross-section view of an example skin-mountable device while mounted to the surface of an arm.
Figure 2B:
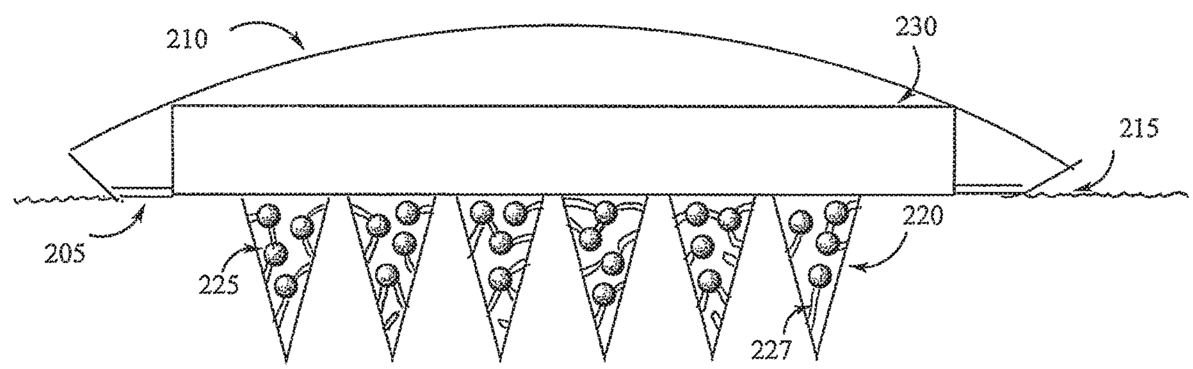
FIG. 2B is a side cross-section view enhanced to show the assay component of the example skin-mountable device when mounted as shown in FIG. 2A.
Figure 2C:
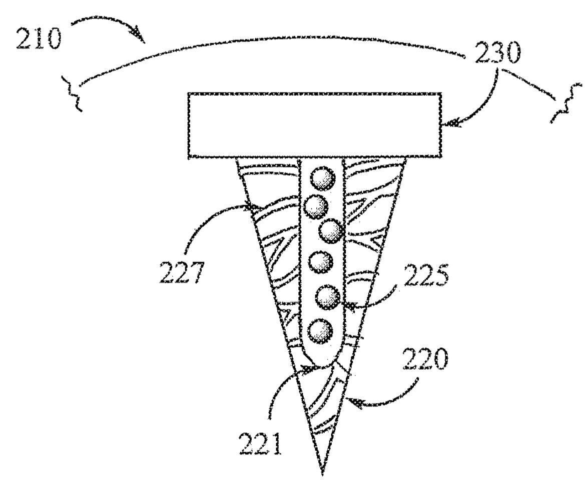
FIG. 2C is a side cross-section view enhanced to show another embodiment of an assay component of the example skin-mountable device when mounted as shown in FIG. 2A.
Figure 3:
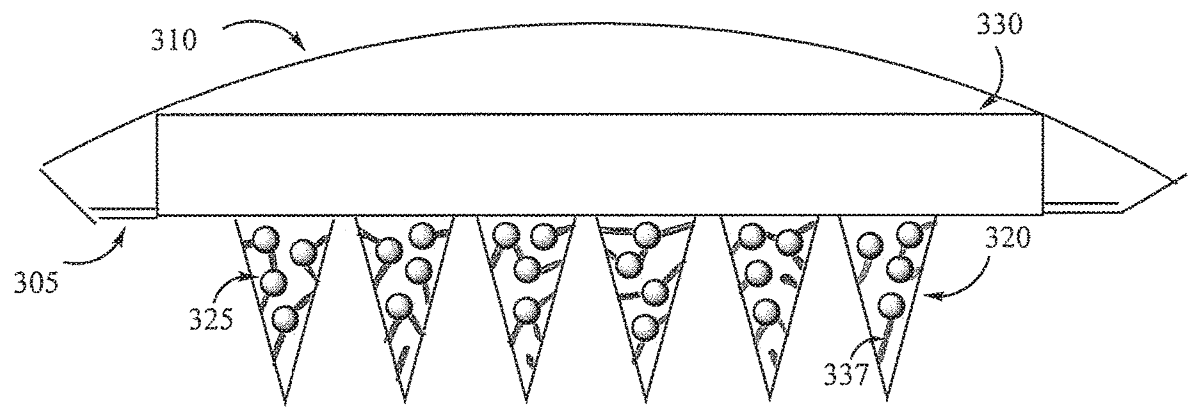
FIG. 3 is a side cross-section view enhanced to show a further embodiment of an assay component of the example substrate.

FIG. 2A shows the cross-sectional views of 200 with the substrate 210 mounted on the skin 205 with an inward-facing surface 232 and an outward-facing surface 234. It is noted that relative dimensions in FIG. 2A are not necessarily to scale, but have been rendered for purposes of explanation only in describing the arrangement of the example skin-mountable substrate 210. The substrate 210 can have an optode nanosensor as assay component 230 configured to undergo an optically-detectable change upon interaction with an analyte. In some examples, the optically-detectable change may involve a change in optical absorption, reflectivity, and/or fluorescence. The assay component 230 may be attached or partially embedded in substrate 210. FIG. 2B illustrates a cross sectional view of an embodiment of a substrate 210 including porous micro-needles 220, attached to substrate 230, where the nanosensors 225 are encapsulated in the micro-needles. Channels 227 allow interstitial fluid to diffuse into the micro-needles 220 and interact with the nanosensors 225. FIG. 2C illustrates a cross sectional view of another embodiment of a porous micro-needle device 210 including micro-needle 222, attached to substrate 230, having an interior hollow space or cavity 221 where the nanosensors 225 in a hydrogel matrix are contained in the hollow cavity 221. Channels 227 allow interstitial fluid to diffuse into the hollow cavity 221 of micro-needle 222 and interact with the nanosensors 225. FIG. 3 illustrates a cross sectional view of an embodiment of a substrate 310 including solid micro-needles 320, attached to substrate 330, where the nanosensors material 325 are embedded or encapsulated within a solid micro-needles 320. The sacrificial agent 327 (solid lines) is dispersed throughout the solid micro-needles 320. Following implantation into skin, the interstitial fluid leaches out at least a portion of the sacrificial agent to produce porous micro-needles in situ as shown in FIG. 2B where removal of the sacrificial agents produces channels 227. Various micro-needle types and nanosensors can be used in different combinations within a device array.

In one embodiment, the micro-needle device provides a single-use collection means. In this design, the micro-needle array device is used to extract a single or series of measurements over a period of time and then is detached from the skin and disposed of. Sensing information or signals can be transferred optically, e.g., refractive index or fluorescence.

The micro-needle can function as a conduit for fluids, solutes, electric charge, light, or other materials. In one embodiment, micro-needles can have a interior hollow space filled with a substance, such as a gel, that has a sensing functionality, e.g., nanosensors, associated with it. In an application for sensing based on the binding of a substrate or reaction mediated by an enzyme, the substrate or enzyme or both can be immobilized in the needle.

c. Optode Nanosensors

In one embodiment, the optode nanosensors can emit light, e.g., fluorescence, at different intensities in the presence of a target analyte, such as glucose. As indicated above, the analyte can be any biomolecule or ion of interest, e.g., glucose, sodium, potassium, calcium, chloride, or a combination thereof. Suitable but non-limiting examples of nanosensors suitable for use in the devices, systems, and methods as described herein are described in Balaconis et al., Biodegradable optode-based nanosensors for in vivo monitoring. *Anal Chem.* 2012 Jul. 3; 84(13):5787-93, which is hereby incorporated by reference in its entirety. Additional nanosensors suitable for use in the present system and methods include, copper and copper oxide nanowires, porous films as well as nanoflowers and nanorods, nanostructured copper oxide/copper oxalate, nanoparticles composed of silver, gold, nickel, and nickel/palladium, such as gold nanowires, nickel hydroxide nanocomposites, boron-doped diamond nanorods, platinum/lead nanoporous networks, palladium nanoparticles, polymeric nanoparticles, and fluorescent polymeric nanosensors. See, e.g., Cash and Clark, Trends Mol Med. Sep. 23, 2010; 16(12): 584-593, which is incorporated herein by reference.

Fluorescent polymeric nanosensors are particularly useful in detecting target analytes such as $Na^{+}$, $K^{+}$, $Cl^{-}$, glucose, urea, creatinine, and bicarbonate. Fluorescent nanosensors are a modular family of sensors that can continuously monitor in vivo physicoloical parameters, including by not limited to oxygen, pH, ammonia, nitrate, nitrite, and sulfate. The sensors are approximately 100 nm in diameter, and specific nanosensor formulation can emit a reversible, concentration-dependent fluorescent signal.

In one embodiment, the nanosensor can be a sensor material comprised of a (i) quantum dot or a fluorescent dye as a signal source that fluoresces at a first wavelength, (ii) a chromophore that absorbs photons of a first wavelength in one state and does not absorb photons of the first wavelength in a second state, and (iii) an ionophore which selectively associates with specific ions or groups of ions, all which are embedded in a polymer including a plasticizer. An additive, e.g., optically-inactive hydrophobic charge-carrying molecule, for facilitating ion exchange within the sensor's hydrophobic core and providing charge neutrality within the sensor may be included. The polymer imparts mechanical stability while the plasticizer allows the three encapsulated sensing components to diffuse within an individual nanoparticle. In monitoring ionic analytes, the chromoionophore changes state in response to proton concentration, e.g, the protonated chromoionophore is one state while the deprotonated chromoionphore is a second state. To monitor a specific analyte, an ionophore that selectively associates with specific ions or group of ions is included in the nanosensor. Once the ionophore associates with a cationic analyte, e.g., Na+ associates with a Na+ selective ionophore, for instance, protons are displaced from the sensor to equilibrate charge, altering the state of the chromoionophore. The fluorescence emitted from the nanosensor indicates the state of the chromoionophore which correlates to the presence and/or concentration of the ionic analyte. For a review of fluorescent polymeric nanosensors and methods of preparation, see U.S. Pat. No. 8,263,358; PCT/US2013/029396; Balaconis et al, Anal. Chem., 2012, Vol. 84(13), pp. 5787-5793; Clark et al., Mikrochim. Acta 131, pp. 121-128 (1999); Monson et al. "PEBBLE nanosensors for in vitro bioanalysis" (www.umich.edu/~koplab/reseach2/CRC_Review_try3pr.pdf); Billingsley et al, Anal. Chem, (2010), Vol. 82(9), pp. 3707-3713 (doi: 10.1021/ac100042e) which are incorporated by reference in their entirety.

In one embodiment, nanosensors that are biocompatible and biodegradable and that do not induce an inflammatory response upon implantation into tissue are provided. As the intradermal environment is one of the most immunogenic tissues in the body, implantation of nanosensors will most likely induce an inflammatory response and subsequent fibrotic tissue deposition to form a fibrotic capsule which could severely affect the performance of the nanosensors. Depending on the implantation time-frame, the formation of a fibrotic capsule can dampen the fluorescence signal to the detector as well as and decrease the diffusion of ions or other analytes that reach the nanosensors. Therefore, biocompatible and biodegradable materials are desired in manufacturing the nanoparticles. Furthermore, such materials can be hydrophobic and/or with degradation products that do not alter the local pH. Suitable but non-limiting example of sensor material that can be used to make biocompatible/biodegradable nanosensors include polycaprolactone (PCL), pluronics (F-127) and citroflex, a citric acid based plasticizer. For a description of suitable sensor material for making biocompatible/biodegradable nanosensors for in vivo use can be found in Balaconis et al., Anal Chem. 2012 Jul. 3; 84(13):5787-93, which is incorporated by reference in its entirety.

In one embodiment, the polymer is biocompatible. The term biocompatible polymers includes polymers that are neither themselves toxic to the host, e.g., a cell, human, or animal) nor degrades at a rate that produces monomeric or oligomeric subunits or byproducts at toxic concentrations to the host. Representative examples of suitable biocompatible polymers include, without limitation, poly (caprolactone) (PCL), ethylene vinyl acetate polymer (EVA), poly(ethylene glycol) (PEG), poly(vinyl acetate) (PVA), poly(lactic acid) (PLA), poly(glycolic acid) (PGA), poly(lactic-co-gylcolic acid) (PLGA), chitosan, alginate, polylysine, collagen or mixtures thereof. In this embodiment, a biocompatible plasticizer may be used with the polymer and includes materials which are soluble or dispersible in the relevant polymer which increases the flexibility of the polymer matrix, and which, in the amounts employed, are biocompatible. Suitable plasticizers include, without limitation, dioctyl sebacate (DOS), poly(glycerol sebacate) (PGS), and acetyl tri-n-butyl citrate. Representative examples of suitable polymers and plasticizers include those described in U.S. Pat. Nos. 2,784,127; 4,444,933; and 8,263,358.

In another embodiment, florescence nanosensors are combined with a catalytic agent that catalyzes a reaction in which a target substrate and/or a co-substract is converted into one or more products. This expands the range to detectable target analytes to include biological molecules such as glucose. This is embodiment, the target can be the target substrate, the co-substrate, or at least one of the one or more products and the nanosensor is sensitive to the analyte such that the nanosensor emits a fluorescent signal upon detecting the analyte. In one embodiment, the catalytic agent is an enzyme. Non-limiting representative examples of catalytic agents include glucose oxidase, diamino oxidase, acetylcholine esterase, cholesterol oxidase or glutamate dehydrogenase. Enzyme-based sensors can recognize a broad range of target substrates with high recognition specificity such as glucose. In one embodiment, the enzyme is an oxidase. For instance, glucose oxidase catalytically oxidizes glucose into gluconic acid, which lowers the pH, and the measured pH change based on optical emission correlates to glucose concentration. In some embodiments, the nanosensor and catalytic agent can be embedded in a polymer matrix such as a hydrogel. Cofactors and other components support the catalytic agents can be included.

In another embodiment, the catalytic agent can be a non-enzymatic protein. In another embodiment, the catalytic agent is a non-biological component such as lipohilic boronic acid derivatives that can serve as a glucose recognition elements. See, for instance, Billingsley et al. *Anal. Chem.* (2010), Vol. 82(9), pp. 3707-3713.

The nanosensor materials can be sized or shaped into any suitable configurations that can be achieved using the polymer. The sensor materials can be spun, sprayed or evaporated onto any surface of the micro-needles including the outside surface wall or interior surface of the micro-needles to produce a coating including the nanosensors.

In another embodiment, the nanosensor may include a targeting moiety such as a member of a specific binding pair such as a ligand, a receptor, an antibody or aptamer. In some embodiments, the targeting moiety can be bound to the polymer matrix.

Nanosensors which target different molecules and are excited by different wavelengths of light can be used in the same sensor to allow for detection of multiple analytes. Thus, in certain aspects, the disclosure provides micro-needles comprising comprising one or more analyte-sensitive nanosensors. In one embodiment, two or more types of nanosensors can be used, each having a different emission wavelength. In still another embodiment, each type of nanosensor has a different excitation and emission wavelength. By designing the nanosensors with this feature, the real time measurement of different target molecules/ions can be obtained with one substrate. That is, using different excitation wavelengths of light, the concentration of different target molecules/ions can be quantified at different times or at approximately the same time. As an added advantage, this allows charting of different measured values at the same time and at a cost savings.

Figure 4:
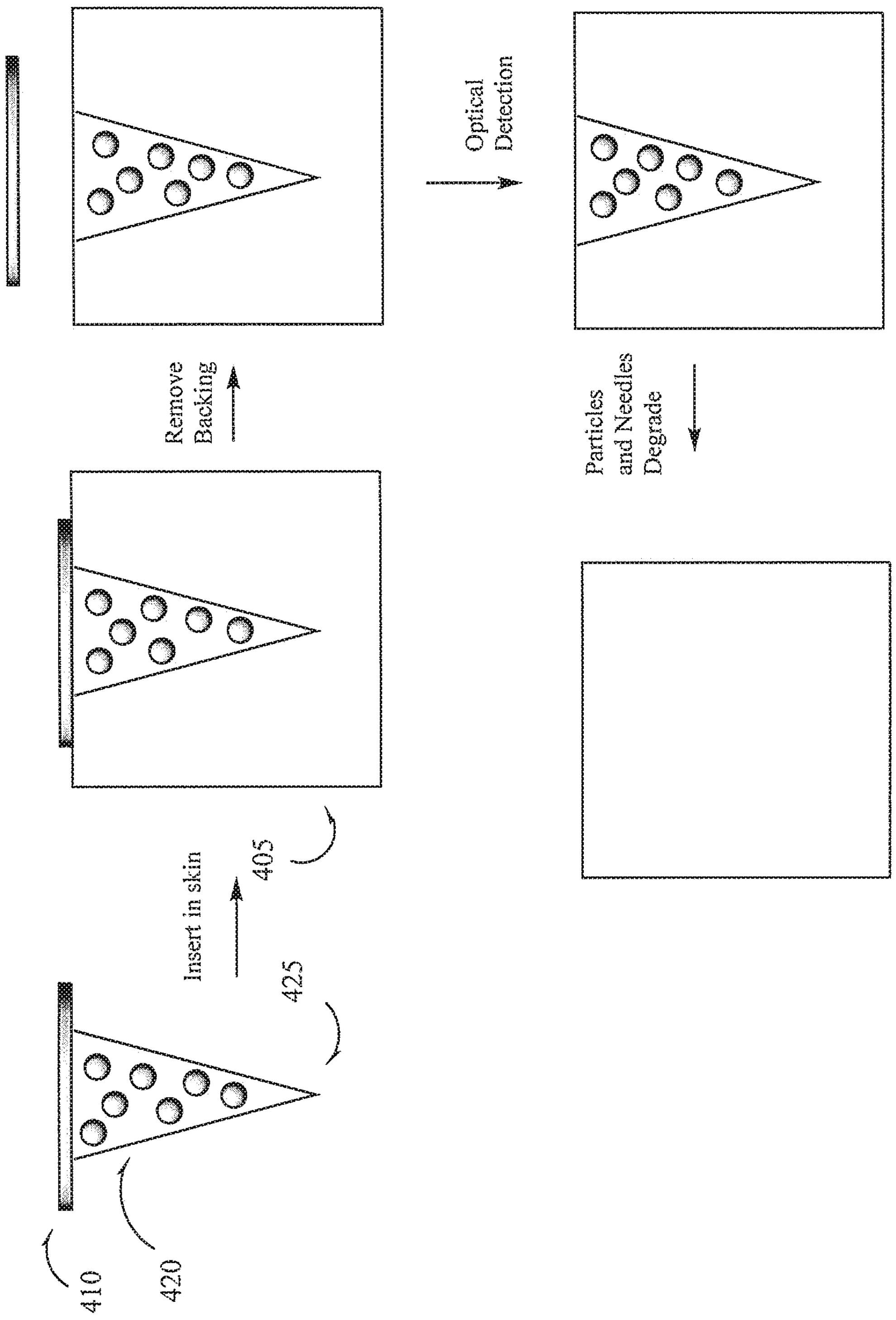
FIG. 4 is a side cross-section of a view enhanced to show the assay component of an example skin-mountable device when mounted as shown in FIG. 2A.

In another embodiment, the micro-needles and the nanosensors can be comprised of a biodegradable material, e.g., PLGA, that degrades at a slower rate relative to the nanosensors. The interface between the micro-needles and the adhesive backing can be comprised of a water-soluble material (PVA or PAA) such that after the micro-needles patch has been applied, water can then be applied to dissolve the water-soluble adhesive material so that the patch can be removed, leaving the micro-needles in the skin. Representative examples of water-soluble adhesive include, PVac adhesives, polyvinayl alcohol, cellulose ethers, methyl cellulose, carboxymethylcellulose, polyvinylpyrrolidone, dextrins, starches, casein, soybean, milk albumin, skin (e.g., animal hides) adhesives, and fish adhesives. FIG. 4 illustrates a porous micro-needle(s) having encapsulated nanoparticles bound to an water soluble adhesive layer between the micro-needle(s) and the substrate 410. Following the application of the skin patch into skin 405, water is applied and the adhesive layer dissolves, releasing the substrate 410 from the micro-needle(s) array 420. After one or measurements of targets are made, both the nanosensors and micro-needles degrade and are absorbed by the body. The nanosensors and micro-needles can have any suitable degradation rate. Typically, the nanosensors and micro-needles can degrade in one or two weeks, depending the selection of polymers used in manufacture.

d. Collection Chamber

In one embodiment, an optional fluid collection chamber can be included to collect interstitial fluid. The fluid collection chamber is selectably in connection with the micro-needle bores or pores, such that interstitial fluid can flow from the tissue surrounding the micro-needle, through the micro-needle, and into the collection chamber. Typically, the collection chamber is attached to, or integrated into, the substrate. The chamber should function to contain a biological fluid sample so as to permit analysis within or on the micro-needle device.

The collection chamber can be substantially rigid or readily deformable. The collection chamber can be formed from one or more polymers, metals, ceramics, semiconductor, or combinations thereof. In a preferred embodiment, the collection chamber contains a porous or absorbent material, such as a sponge, gel, or paper or polymeric strip. The material can be permanently contained or removable, and can function as a separate diagnostic element or substrate for use in analytical devices. The chamber can initially be empty or can contain a gas or one or more reagents in any form (e.g., liquid or solid particles).

In one embodiment, the collection chamber is formed of an elastic material, such as an elastomeric polymer or rubber. For example, the collection chamber can be a collapsed balloon-like pouch that expands when the biological fluid is drawn into the collection chamber.

In another embodiment, the collection chamber of a micro-needle device can include a plurality of compartments that are temporarily or permanently isolated from one another and/or from a portion of the micro-needles in an array. The device can, for example, be provided to collect or sense through different needles at different rates or at different times into the different compartments.

In a representative example, micro-needles can be formed using a polymer mixture of a sacrificial agent, e.g., gelatin (10% w/v), poly (ethylene oxide) ("PEO"), up to 40% w/v, sugar, NaCl or paraffin, and a polymer, e.g. PLLA, pHEMA, PCL, or PGLA. A 10% w/v gelatin solution was dispersed in a 20 mg/ml of sodium alginate. $1\times10^{12}$ nanosensors/ml of nanosensors, prepared by the method of nanoprecipitation (Dubach et al. J. Vis. Exp., Jul. 4, 2011, Vol. 53, pp. 2896, doi 10.3791/2896) is then added to the dispersion. The sugar-polymer-nanosensor mixture is then molded, e.g., standard injection molding or UV lithography, under suitable conditions to form the solid micro-needles by solidifying the continuous polymer phase around the dispersed porogen particles and nanosensors. The porous structures are then formed by immersing the solid micro-needles into a suitable solvent, warm water at a temperature of 37 degrees Celsius, for overnight to leach out the gelatin. The porous structures were then washed and dried in a desiccator. The resulting micro-needles would have an optically clear, biocompatible and/or bio-degradable porous structure including encapsulated nanosensors.

IV. Example Optical Sensor

As shown in the cross-sectional views 200, 202 and 204 in FIGS. 2A, 2B and 2C, the substrate 210 can be mounted on the skin 205 with an inward-facing surface 232 and an outward-facing surface 234. It is noted that relative dimensions in FIG. 2A are not necessarily to scale, but have been rendered for purposes of explanation only in describing the arrangement of the example skin-mountable substrate 210. The substrate 210 can have an optode nanosensor as assay component 230 configured to undergo an optically-detectable change upon interaction with an analyte. In some examples, the optically-detectable change may involve a change in optical absorption, reflectivity, and/or fluorescence. At least a portion of assay component 230 may be embedded in a polymeric material.

As shown in FIG. 2B, the assay component 230 may extend from the inward-facing surface 232 such that the assay component 230 is in direct contact with the skin 205 and penetrates into the intradermis 215 of the skin so as to contact interstitial fluid. In this way, the assay component 230 can interact with an analyte in the interstitial fluid of the skin 205. In some embodiments, the substrate 210 can include a micro-needle array 220, which includes optode nanosensors 225 embedded or encapsulated with the polymeric micro-needles, protruding into the intradermis 215 of the skin 205 to enable the assay component 230 to interact with an analyte in the interstitial fluid 270 of the skin 205.

Assay component 230 can be selectively sensitive to an analyte by including a catalytic reagent such as an enzyme, specific binding agents such haptens, antibodies, or aptamers, and other reagents that selectively interacts with the analyte. A sensitizing layer or coating can be located proximal to the nanosensor 225 of assay component 230. The sensitizing layer can include elements other than elements that selectively interact with the analyte; for example, the sensitizing layer could include a polymer that is permeable to the analyte. An analyte-selective element of the sensitizing layer could be encapulated in, adsorbed onto, covalently bonded to, or otherwise disposed on or within such a polymer.

In some examples, the sensitizing layer can include one or more ionophores that selectively interact with an ion. In some examples, the ion is potassium, and the ionophore includes one or more of valinomycin, bis[(benzo-15-crown-4)-4'-ylmethyl]pimelate), 2-dodecyl-2-methyl-1,3-propanediyl-bis-[N-(5 '-nitro(benzo-15-crown-5)-4'-yl)carbamate], and 4-tert-butyl-2,2,14,14-tetrahomo-4a,14a-dioxacalix[4]arene-tetraacetic acid tetra-tert-butyl ester. Potassium from the interstitial fluid can diffuse into the micro-needles 225 and reversibly bind to the ionophore, resulting in an optical change that can be measured by a photodetector.

A protective layer which is permeable to the analyte can be disposed on the sensitizing layer. The protective layer can be composed of a polymer that is permeable to the analyte. The polymer may be formulated to include porogens to tailor the permeability to the analyte of the protective layer for a specific application. In some examples, the sensitizing layer could be selectively sensitive to one or more analytes in addition to the analyte of interest. In those examples, the protective layer could be configured to be impermeable to the one or more analytes, such that only the analyte of interest was able to both diffuse through the protective layer and interact with the sensitizing layer.

The assay component 230 can include components that allow for the optical detection of a select analyte by a reader. For example, the assay component may include assay components that undergo a detectable change, e.g., in optical absorption, reflectivity or fluorescence, upon interaction with an analyte. In such embodiments, the reader may be placed over the substrate and measure the analyte by detecting the change in optical property. The reader device may include a excitation light source configured to direct light toward the substrate, and a photodetector configured to detect light emission from the substrate.

The system may further include one or more data collection systems for interrogating, in a non-invasive manner, the nanosensor. In one example, the system includes a detector configured to detect a response signal transmitted from the sensor. The response signal can include both an analyte response signal, which can be related to the interaction of the one or more target analytes with the nanosensor, and a background noise signal. For example, the nanosensor may include a fluorescent labels configured to produce a fluorescence signal in response to a chemical reaction initiated, at least in part, to the presence of the target analyte.

In some examples, the system may include an interrogating signal source for transmitting an interrogating signal in the form of an excitation light that can penetrate into the sensor following exposure to the analyte and a detector for detecting a response signal that is transmitted from the sensor, in response to the interrogating signal. The interrogating signal can be any kind of optical signal that results in a response signal that can be used to measure a physiological parameter or, more particularly, that can detect the binding or interaction of the clinically-relevant analyte to the sensor. In one example, where the sensor includes fluorescence nanosensors, the interrogating signal is an optical signal with a wavelength that can excite the fluorophore in the sensor (e.g., a wavelength in the range of about 500 to about 1000 nanometers), and the response signal is fluorescence radiation from the fluorophore that can reach the detector.

In some cases, an interrogating signal is not necessary to measure one or more of the physiological parameters and, therefore, the wearable device 100 may not include a signal source 170. For example, the nanosensors can include an autofluorescent or luminescent marker, such as a fluorophore, that will automatically emit a response signal indicative of the binding of the clinically-relevant analyte to the nanosensors, without the need for an interrogating signal or other external stimulus. In some examples, the nanosensors may include a chemiluminescent marker configured to produce a response signal in the form of luminescence radiation produced in response to a chemical reaction initiated, at least in part, to the binding of the target analyte to the particle.

Additionally, the system may further include a modulation source configured to modulate the analyte response signal. The modulation source can be configured to modulate the analyte response signal differently than the background noise signal. To this end, the modulation may help to discern between the target analyte and, essentially, everything else in the body by, for example, increasing the signal-to-noise ratio. Generally, the modulation may include any spatial, temporal, spectral, thermal, magnetic, mechanical, electrical, acoustic, chemical, or electrochemical, etc. modulation technique or any combination thereof.

In some scenarios, it may also be useful to detect and distinguish both the analyte response signal—related to nanosensor bound to or interacting with target analyte(s)—and an "unbound" nanosensor signal—related to nanosensors bound to or interacting with target analyte(s). For example, in some measurement or characterization schemes, it may be useful to determine the percentage of nanosensors present in the sensor that have bound to the target analyte. In such cases, the modulation source may be configured to modulate the analyte response signal differently than the unbound nanosensor signal.

The elements of the system, namely the type of modulation, the types of nanosensors and target analytes may all be interrelated. Ultimately, the type of nanosensors used to detect a particular target analyte may depend, to some extent, on the characteristics of the target analyte (i.e., type, size, shape, affinities, etc.) and the chosen type of modulation (i.e., spatial, spectral, thermal, magnetic, mechanical, chemical, etc.).

V. Example Substrate/Reader Interactions

Figure 5A:
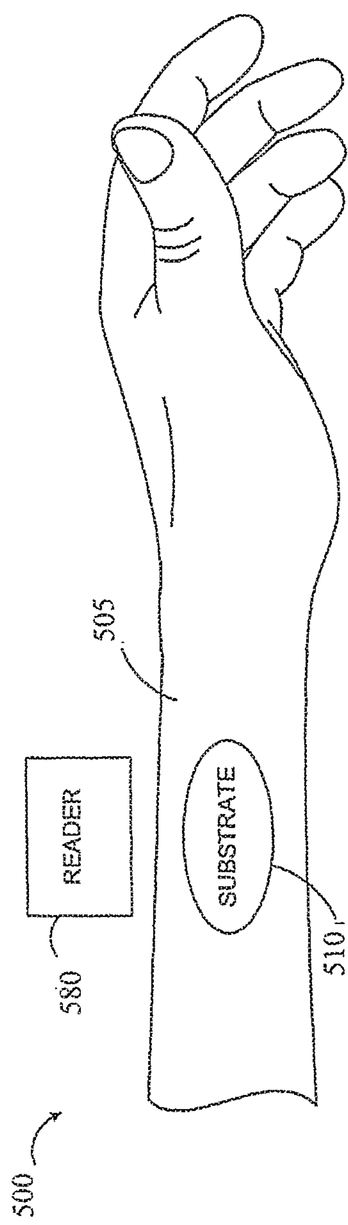
FIG. 5A is an example system that includes a skin-mountable device and a proximate reader, in accordance with an example embodiment

FIG. 5A is a diagram of an example system 500. The substrate 510 is mounted on a surface of skin 505 (i.e., a skin-mounted substrate) and an external reader 580 is positioned proximate to the substrate 410. It is noted that relative dimensions in FIG. 5A are not necessarily to scale, but have been rendered for purposes of explanation.

Figure 5B:
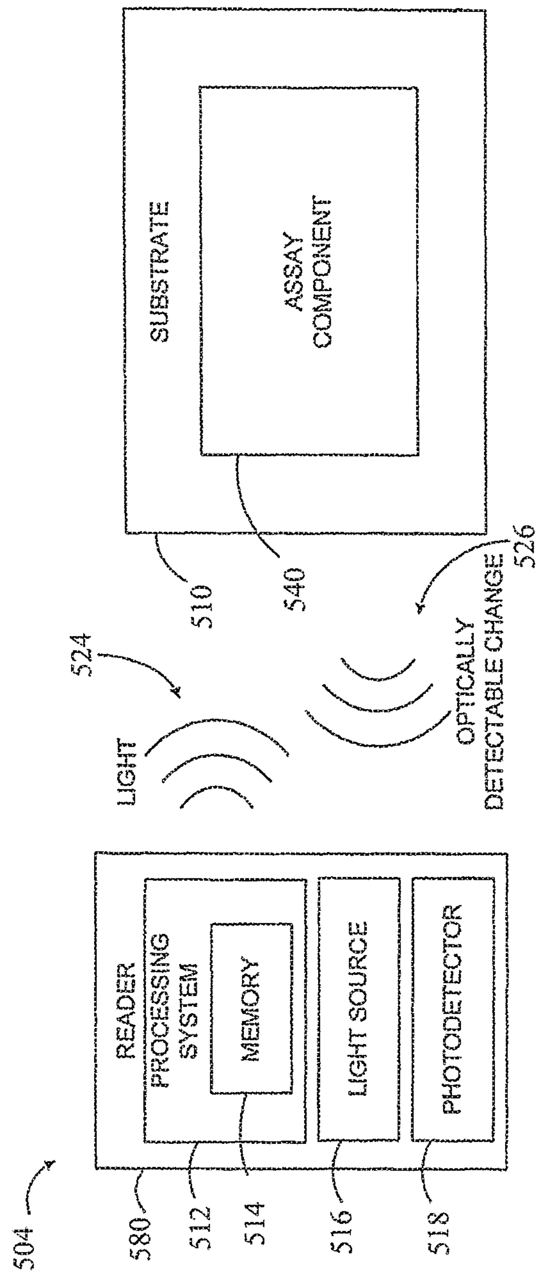
FIG. 5B is a block diagram of a skin-mounted optical sensor system operated by a reader device capable of detecting an optically-detectable change in a substrate, in accordance with an example embodiment.

In one embodiment, the substrate 510 may include optode nanosensors as an assay component 540. FIG. 5B is a block diagram of a system described in connection with substrate 510 and reader 580 in FIG. 5A. System 504 includes a substrate 510 operated by a reader 580 to obtain one or more measurements related to an analyte in interstitial fluid of the skin. An assay component 540 configured to undergo an optically-detectable change 526 related to the analyte can be included with substrate 510. The optically-detectable change 526 may include a change in at least one of optical absorption, reflectivity, or fluorescence. As shown in FIG. 5A, substrate 510 is configured to be contact-mounted over an external skin surface 505.

The skin-mounted assay component 540 can be operated to a light source from the reader 580. The reader 580 may include a light source 516 configured to direct light 524 toward the assay component 540 of the substrate 510, and a photodetector 518 configured to detect light 526 from the assay component 540. For example, the substrate 510 may include nanosensors as an assay component 540 that fluoresces upon interaction with an analyte. The reader 580 may be placed proximate to the substrate 510 so that the light source 516 may provide light 524 to the assay component 540. If the analyte is present, the assay component 540 may fluoresce, and the fluorescence 526 may be detected by the photo detector 518.

In other embodiments, sensor 530 can further include and/or be replaced by sensor(s) that measure light, heat/temperature (e.g., body temperature), blood pressure, air flow, altitude, and/or other characteristics than analyte concentration(s). In these other embodiments, sensor 530 can communicate data about the measured characteristics to reader 480 using backscatter communication 522.

VI. Example Readers

The system includes a reader device ("reader") that is configured to detect the interaction between the substrate and the analyte in the interstitial fluid. The reader can be a smart phone, digital assistant, or other portable computing device with wireless connectivity sufficient to communicate with the substrate. The function of the reader can be included in a "wearable device." The term "wearable device," as used in this disclosure, refers to any device that is capable of being worn at, on or in proximity to a body surface, such as a wrist, ankle, waist, chest, or other body part, e.g., an eye-glass frame, a head-mountable computer frame, a cap, a hat, part of a hat or cap (e.g., a hat band or bill of a baseball cap), a headphone headband, a watch, etc. In some examples, the reader is positioned proximate to the substrate only when a measurement is desired. In other examples, the reader is mounted proximate to the substrate so that the analyte-substrate interaction can be detected on demand or continuously without having to position the reader.

Figure 6A:
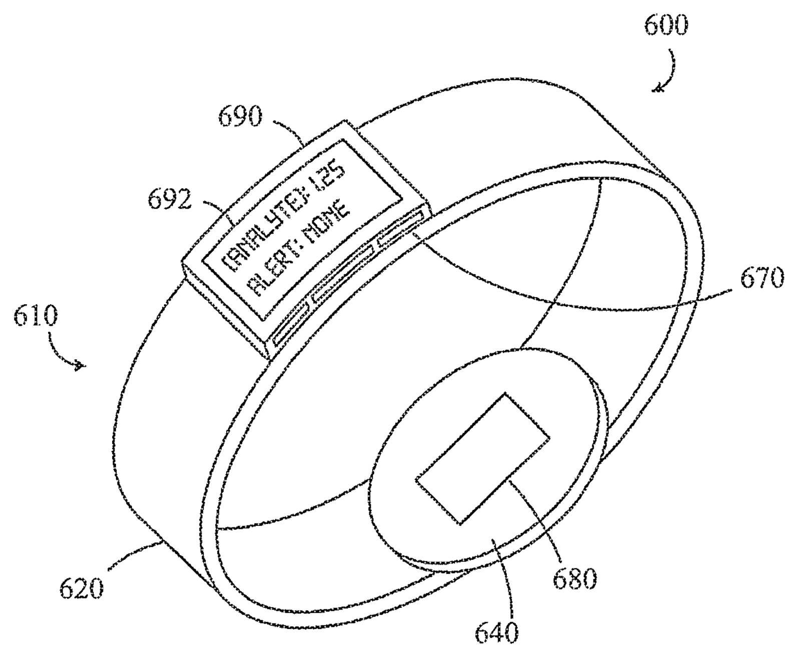
FIG. 6A is an example reader included in a wearable device in accordance with an example embodiment
Figure 6B:
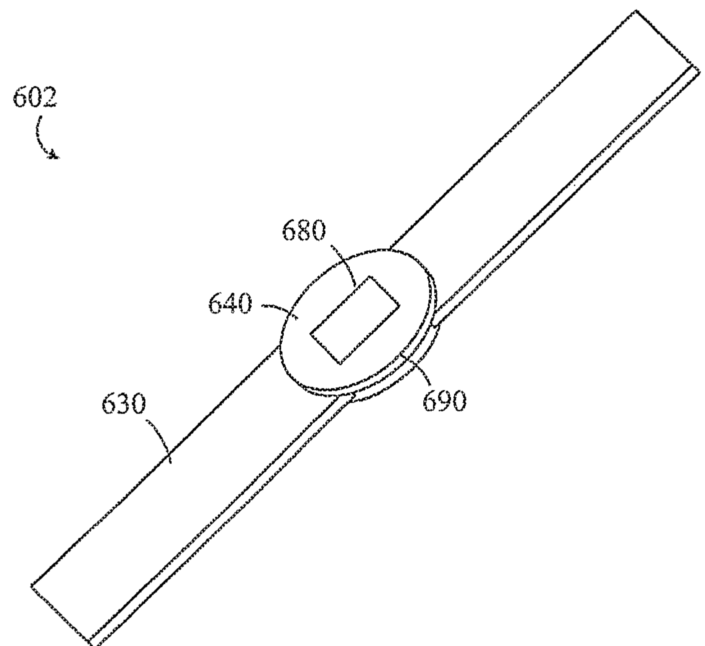
FIG. 6B is an example reader included in a wearable device in accordance with an example embodiment

FIGS. 6A and 6B show example wearable devices 600 and 602. The device may be placed in close proximity to the substrate, but need not be touching or in intimate contact therewith. A mount 610, such as a belt, wristband, ankle band, etc. can be provided to mount the device at, on or in proximity to the body surface. The mount 610 may prevent the wearable device from moving relative to the body to reduce measurement error and noise. In some embodiments, the wearable device is placed directly over the substrate. In one example, shown in FIG. 6A, the mount 610, may take the form of a strap or band 620 that can be worn around a part of the body. Further, the mount 610 may be an adhesive substrate for adhering the wearable device 600 to the body of a wearer.

A reader platform 640 is disposed on the mount 610 such that the reader platform 540 can be positioned proximate to the substrate. The reader platform 640 may house the reader components 680 shown in FIG. 1. The wearable device 600 may also include a user interface 690 via which the wearer of the device may receive one or more recommendations or alerts generated either from a remote server or other remote computing device, or from a processor within the device. The alerts could be any indication that can be noticed by the person wearing the wearable device. For example, the alert could include a visual component (e.g., textual or graphical information on a display), an auditory component (e.g., an alarm sound), and/or tactile component (e.g., a vibration). Further, the user interface 690 may include a display 692 where a visual indication of the alert or recommendation may be displayed. The display 692 may further be configured to provide an indication of the measured physiological parameters, for instance, the concentration of a measured analyte.

In another embodiment, as shown in FIG. 6B, the reader platform 640 may be positioned on the back side of the user interface 690.

In some embodiments, a reader can power a sensor in the substrate using a low-power transmission; e.g., a transmission of 1 watt or less of power. In these embodiments, the reader can be within a predetermined distance; e.g., 1 foot, 40 cm, of the substrate.

After receiving analyte-related data from the substrate, the reader can utilize the data; e.g., process, present, store, communicate, etc. For example, the reader can process the analyte-related data to generate an analyte concentration, and the display device can present the analyte concentration to the user.

In some embodiments, the reader may evaluate the analyte-related data and display a visual indication of an alert or recommendation and/or an indication of the measured physiological parameters. For example, the reader may compare an analyte concentration to a low- and/or high-analyte threshold(s) to determine, respectively, whether the analyte concentration is too high or low for the wearer of the system. If the blood-glucose data is too high or low for wearer, the display can alert wearer, attempt to contact another person or entity to help the wearer, and/or perform some other action.

Further, the user interface 690 may include one or more buttons 670 for accepting inputs from the wearer. For example, as shown in FIG. 6A, the buttons 670 for accepting inputs from the wearer. The buttons 670 may be configured to change the text or other information visible on the display 692. The buttons 670 may also be configured to accept inputs for controlling aspects of the data collection system, such as initiating a measurement period, or inputs indicating the wearer's current health state (i.e., normal, migraine, shortness of breath, heart attack, fever, "flu-like" symptoms, food poisoning, etc.).

VII. Example Operations

In some embodiments, the present disclosure provides a method for operating a system including a substrate and a reader to measure an analyte concentration of a fluid in the skin.

Figure 7:
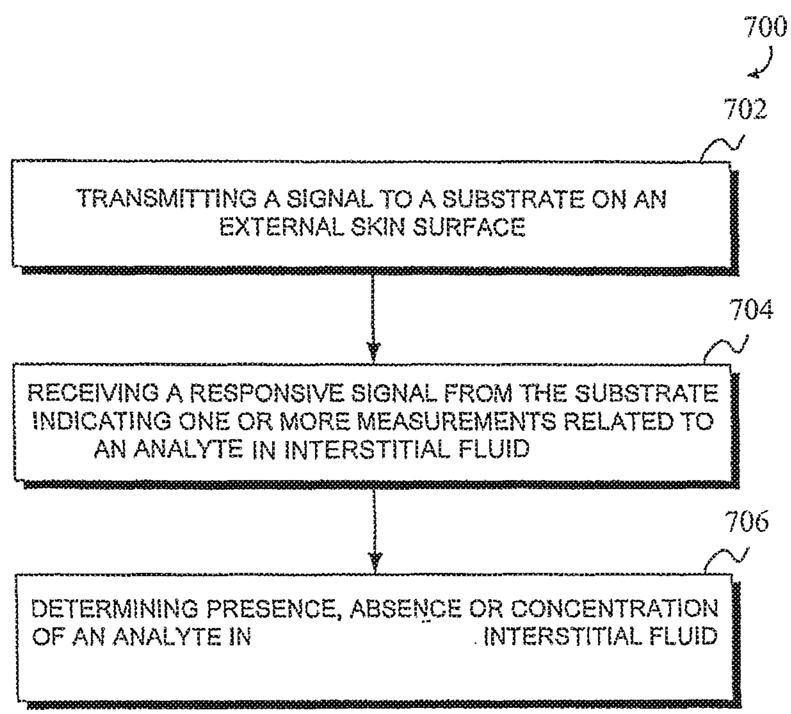
FIG. 7 is a flowchart of an example method for operating a system with an external reader and a skin-mounted substrate to measure an analyte in a fluid in the skin.

FIG. 7 is a flowchart of a method 700 for operating a system including a reader and a substrate mounted to an external skin surface to measure an analyte in interstitial fluid in the skin. The method includes transmitting a signal to a substrate on an external skin surface (702). In some examples, the substrate includes an antenna and the signal is a radio frequency (RF) signal. In other embodiments, the signal may be optical, such as visible light or fluorescent light. The method further includes receiving a responsive signal from the substrate (704). The responsive signal may indicate one or more measurements related to an analyte in the interstitial fluid. For example, when the substrate includes an antenna, the responsive signal may be a radio frequency (RF) signal. In other examples, the responsive signal may be an optical signal, such as a change in optical absorption, reflectivity, or fluorescence. In some embodiments, the method may further include determining the presence, absence or concentration of an analyte in the interstitial fluid (706). In embodiments where the substrate includes an electrochemical sensor selectively sensitive to an analyte, the concentration of the analyte may be determined. In embodiments where the substrate includes a component configured to undergo an optically-detectable change related to an analyte, the presence, absence or concentration of the analyte, may be determined.

VIII. Conclusion

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims.

The above detailed description describes various features and functions of the disclosed systems, devices, and methods with reference to the accompanying figures. In the figures, similar symbols typically identify similar components, unless context dictates otherwise. The example embodiments described herein and in the figures are not meant to be limiting. Other embodiments can be utilized, and other changes can be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

With respect to any or all of the ladder diagrams, scenarios, and flow charts in the figures and as discussed herein, each block and/or communication may represent a processing of information and/or a transmission of information in accordance with example embodiments. Alternative embodiments are included within the scope of these example embodiments. In these alternative embodiments, for example, functions described as blocks, transmissions, communications, requests, responses, and/or messages may be executed out of order from that shown or discussed, including substantially concurrent or in reverse order, depending on the functionality involved. Further, more or fewer blocks and/or functions may be used with any of the ladder diagrams, scenarios, and flow charts discussed herein, and these ladder diagrams, scenarios, and flow charts may be combined with one another, in part or in whole.

A block that represents a processing of information may correspond to circuitry that can be configured to perform the specific logical functions of a herein-described method or technique. Alternatively or additionally, a block that represents a processing of information may correspond to a module, a segment, or a portion of program code (including related data). The program code may include one or more instructions executable by a processor for implementing specific logical functions or actions in the method or technique. The program code and/or related data may be stored on any type of computer readable medium such as a storage device including a disk or hard drive or other storage medium.

The computer readable medium may also include non-transitory computer readable media such as computer-readable media that stores data for short periods of time like register memory, processor cache, and random access memory (RAM). The computer readable media may also include non-transitory computer readable media that stores program code and/or data for longer periods of time, such as secondary or persistent long term storage, like read only memory (ROM), optical or magnetic disks, compact-disc read only memory (CD-ROM), for example. The computer readable media may also be any other volatile or non-volatile storage systems. A computer readable medium may be considered a computer readable storage medium, for example, or a tangible storage device.

Moreover, a block that represents one or more information transmissions may correspond to information transmissions between software and/or hardware modules in the same physical device. However, other information transmissions may be between software modules and/or hardware modules in different physical devices.

The particular arrangements shown in the figures should not be viewed as limiting. It should be understood that other embodiments can include more or less of each element shown in a given figure. Further, some of the illustrated elements can be combined or omitted. Yet further, an example embodiment can include elements that are not illustrated in the figures.

It will be readily understood that the aspects of the present disclosure, as generally described herein, and illustrated in the figures, can be arranged, substituted, combined, separated, and designed in a wide variety of different configurations, all of which are explicitly contemplated herein. While various aspects and embodiments have been disclosed herein, other aspects and embodiments will be apparent to those skilled in the art.

Example methods and systems are described above. It should be understood that the words "example" and "exemplary" are used herein to mean "serving as an example, instance, or illustration." Any embodiment or feature described herein as being an "example" or "exemplary" is not necessarily to be construed as preferred or advantageous over other embodiments or features. Reference is made herein to the accompanying figures, which form a part thereof. In the figures, similar symbols typically identify similar components, unless context dictates otherwise. Other embodiments may be utilized, and other changes may be made, without departing from the spirit or scope of the subject matter presented herein. The various aspects and embodiments disclosed herein are for purposes of illustration and are not intended to be limiting, with the true scope and spirit being indicated by the following claims.

Where example embodiments involve information related to a person or a device of a person, some embodiments may include privacy controls. Such privacy controls may include, at least, anonymization of device identifiers, transparency and user controls, including functionality that would enable users to modify or delete information relating to the user's use of a product.

Further, in situations in where embodiments discussed herein collect personal information about users, or may make use of personal information, the users may be provided with an opportunity to control whether programs or features collect user information (e.g., information about a user's medical history, social network, social actions or activities, profession, a user's preferences, or a user's current location), or to control whether and/or how to receive content from the content server that may be more relevant to the user. In addition, certain data may be treated in one or more ways before it is stored or used, so that personally identifiable information is removed. For example, a user's identity may be treated so that no personally identifiable information can be determined for the user, or a user's geographic location may be generalized where location information is obtained (such as to a city, ZIP code, or state level), so that a particular location of a user cannot be determined. Thus, the user may have control over how information is collected about the user and used by a content server.

The invention claimed is:

1. A device comprising: a plurality of micro-needles, each micro-needle having a base end and a tip, wherein the micro-needles comprise a sacrificial agent, wherein the sacrificial agent is configured to dissolve in interstitial fluid to form channels in the micro-needles; a substrate attached to the base ends of the micro-needles, wherein the substrate is configured for attachment to an external skin surface such that the micro-needles penetrate into the skin to contact interstitial fluid; and nanosensors encapsulated in the micro-needles, the nanosensors comprising nanoparticles having a detectable label and configured to interact with a target analyte present in interstitial fluid.

2. The device of claim 1, wherein the micro-needles are arranged in an array.

3. The device of claim 1, wherein the sacrificial agent is encapsulated in the micro-needles.

4. The device of claim 3, wherein the sacrificial agent comprises a sacrificial sugar.

5. The device of claim 1, wherein the micro-needles include an enclosed hollow space and wherein the nanosensors are encapsulated in a hydrogel present in the enclosed hollow space.

6. The device of claim 1, wherein the detectable label comprises a fluorophore.

7. The device of claim 1, wherein the substrate further comprises an adhesive material for attaching the substrate to the external skin surface, for attaching the base ends of the micro-needles to the substrate, or both.

8. The device of claim 7, wherein the adhesive is water-soluble such that the substrate can be detached from the base end of the micro-needles and from the external skin surface.

9. The device of claim 1, wherein the micro-needles, the nanosensors, or both are biodegradable.

10. The device of claim 1, wherein the micro-needles comprise a biodegradable polymer.

* * * * *